United States Patent [19]

Ajinkya et al.

[11] Patent Number: 5,190,733
[45] Date of Patent: Mar. 2, 1993

[54] HIGH INTERFACIAL AREA MULTIPHASE REACTOR

[75] Inventors: Milind B. Ajinkya, Mendham; Robert M. Koros, Westfield; Barry L. Tarmy, Berkeley Heights, all of N.J.

[73] Assignee: Exxon Research and Engineering Company, Florham Park, N.J.

[21] Appl. No.: 665,637

[22] Filed: Feb. 14, 1991

Related U.S. Application Data

[63] Continuation of Ser. No. 310,182, Feb. 15, 1989, abandoned, which is a continuation-in-part of Ser. No. 235,572, Aug. 24, 1988, abandoned.

[51] Int. Cl.$^5$ .............................. B01F 5/10; B01F 5/20
[52] U.S. Cl. ...................................... 422/231; 261/77; 261/123; 261/36.1; 261/DIG. 75; 422/230; 422/234
[58] Field of Search ............... 422/230, 231, 224, 234; 261/77, 123, 36.1, DIG. 75

[56] References Cited

U.S. PATENT DOCUMENTS

| | | | |
|---|---|---|---|
| 1,180,372 | 4/1916 | Breydel | 422/231 X |
| 3,723,545 | 3/1973 | Nagel et al. | 261/77 X |
| 3,785,779 | 1/1974 | Li et al. | 422/231 |
| 3,938,738 | 2/1976 | Nagel et al. | 261/77 X |

FOREIGN PATENT DOCUMENTS 1239727 7/1971 United Kingdom ....... 261/DIG. 75

Primary Examiner—Robert J. Warden
Assistant Examiner—Amalia L. Santiago
Attorney, Agent, or Firm—Joseph J. Dvorak

[57] ABSTRACT

In its simplest sense, the present invention provides a method for improving the contacting of plural, distinct phases in a vertically disposed vessel containing distinct fluid phases by injecting a stream of dispersed distinct phases together into the phases contained in the vessel at a sufficient velocity to force the fluid in the vessel to circulate downwardly through a central region in the vessel and upwardly in the annular region surrounding the central region.

4 Claims, 1 Drawing Sheet

HIGH INTERFACIAL AREA MULTIPHASE REACTOR

This is a Rule 60 continuation of U.S. Ser. No. 310,182, filed Feb. 15, 1989 (now abandoned), which is a continuation-in-part of U.S. Ser. No. 235,572, filed on Aug. 24, 1988 (now abandoned).

FIELD OF THE INVENTION

The present invention is concerned with improvements in contacting distinct, physical phases such as gases and liquids.

BACKGROUND OF THE INVENTION

There are many commercially important operations in which it is necessary to physically mix plural distinct phases such as gases and liquids. Indeed, reactions between a gas and a liquid are common in the chemical industry. In such processes, it is important to maximize the interfacial area between the distinct phases so as to optimize the rate of reaction, the yield, or the like.

It is an object of the present invention to provide improvements in contacting of plural, distinct phases so as to enhance or improve the chemical processes being conducted.

Another object of the present invention is to provide improvements in absorption and reaction of olefins, either gases or liquids, by sulfuric acid in the hydration of olefins to produce alcohols.

SUMMARY OF THE INVENTION

In its simplest sense, the present invention provides a method for improving the contacting of plural, distinct fluid phases contained in a vertically disposed vessel by axially injecting a stream of the dispersed distinct fluid phases together into the fluid phases contained in the vessel. Importantly, the injected stream is injected with sufficient fluid movement to force the fluid contained in the vessel to circulate downwardly through substantially the central region of the vessel and upwardly in an annular region between the central region and the outer vessel wall.

DETAILED DESCRIPTION OF THE INVENTION

The present invention will be described by referring specifically to the dispersion of a gas like propylene or butene in a liquid like sulfuric acid. However, it should be readily appreciated that the principles and concepts described herein are equally applicable to other processes in which contacting of distinct phases is desired.

Figure 1:
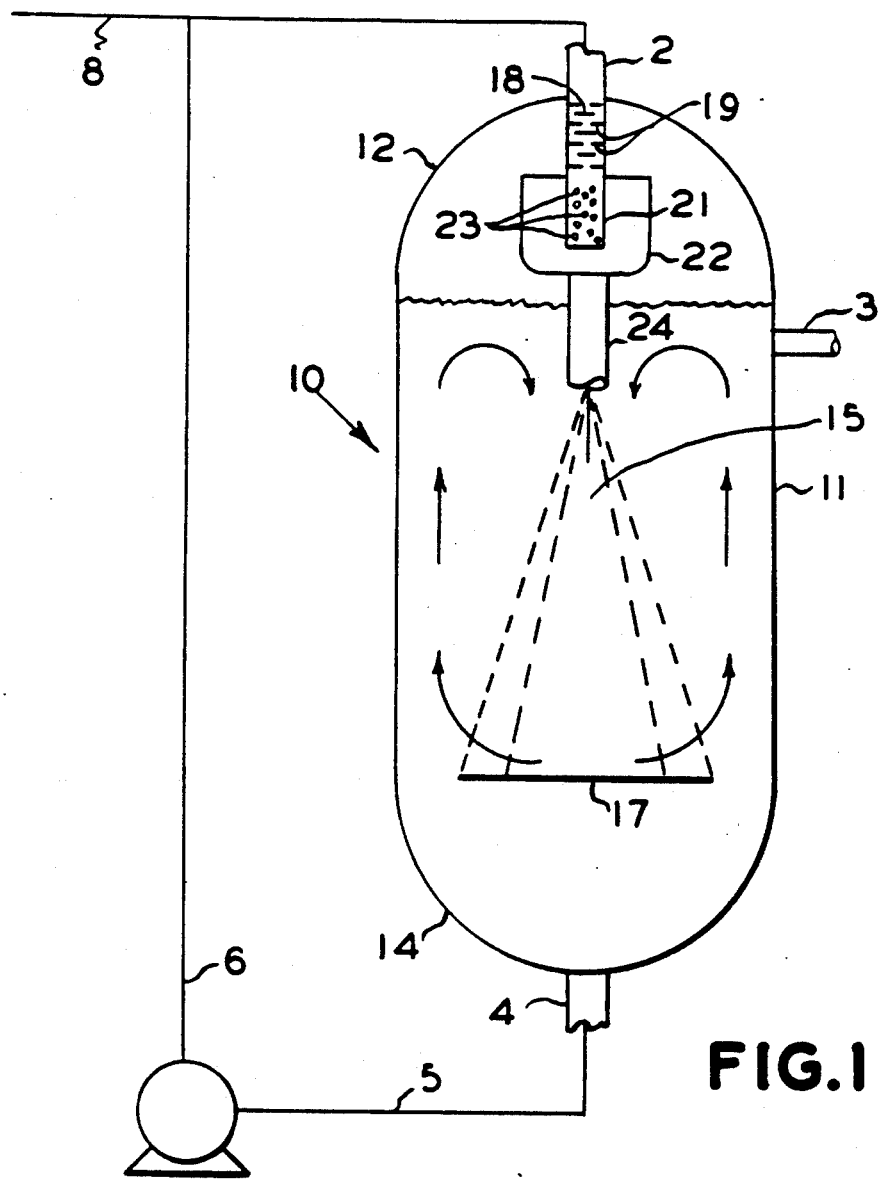
FIG. 1 is a schematic illustration of the present invention.

Turning now to FIG. 1, there is shown a generally cylindrical, vertically disposed vessel 10 having sidewalls 11 and top and bottom walls 12 and 14, respectively. Vessel 10 is also provided with a conduit 4 for removal of liquids for recycle via lines 5 and 6. A conduit 2 is provided for introduction of liquids recycled via lines 5 and 6. Vessel 10 is also equipped with a conduit 3 for removal of liquid product for delivery, for example, to a liquid product store (not shown). Line 8 is provided connecting a gaseous olefin source (not shown) with recycle line 6. Thus, a gaseous olefin and sulfuric acid may be fed together via conduit 2 into the vessel 10.

Conduit 2 contains disk and donut baffles, 18 and 19, respectively, for turning and mixing the gaseous olefin and liquid sulfuric acid as it passes through conduit 2. The mixture of gas and liquid then passes into a pipe 21 centrally positioned in a cylindrical mixing vessel 22. As can be seen, pipe 21 has a plurality of holes 23 for further mixing of the gas and liquid. The fluid then exits the mixing vessel 22 and flows into a nozzle 24 which opens below the level of liquid in the vessel 10.

The nozzle 24 is designed to direct the flow of dispersed gas and liquid phases downwardly substantially in the central region of the vessel. Thus, the flow of dispersed phases ejected from the nozzle will flow outwardly as well as downwardly as shown by the dotted lines. The angle at which the dispersed phases are ejected from nozzle 24 will depend upon a number of factors such as the ratio of the length to diameter of the vessel. In general, however, the angle of ejection of dispersed fluid phases from nozzle 24 will be such that the fluid at its maximum length of downward travel will flow outwardly for a distance between 0.4 to 0.7 times the diameter of vessel 10. The diameter of the nozzle is sufficient to transfer enough momentum from fluid ejected from the nozzle to fluid in its flow path to move from about 3 to about 20 times the amount of fluid ejected. This can be achieved by sizing the nozzle diameter to be from about 1/12 to about 1/20 the length of the vessel.

Located within vessel 10 is a baffle 17 for directing the flow of dispersed fluid radially outwardly. This baffle is positioned substantially normal to the downward flow of fluid ejected from nozzle 24 and placed near the bottom of the vessel. Indeed, it is preferred that the baffle have a diameter of from about 0.4 to about 0.7 times the diameter of the vessel and that it be located at a distance from the vessel bottom that is about 0.2 to about 0.5 times the diameter of the vessel.

In operation then a mixture of the olefin and sulfuric acid is churned and mixed by the baffles in the conduit 2 and fed through holes 23 of pipe 21 causing extremely small bubbles to be formed. The gas and liquid mixture then is emitted as a jet of fluid from nozzle 24 and is injected into the fluid contained in the vessel. The jet of fluid exiting the nozzle exchanges its momentum with the fluid in the central region 15 of the vessel especially the fluid directly in its conical flow path, and causes the fluid in this region to move in substantially a downwardly direction but also in an outwardly direction. This movement in turn causes the entire contents of the vessel to move. This fluid moves upwardly in the annular region between the side walls 11 and the central region 15. As shown, baffle 17 deflects the jet energy of the fluids flowing downwardly, and deflects them radially outwardly preventing the energy from leaving through the recycle exit conduit 4.

In operation, recycle flows are adjusted to give five turnovers of fluid within the vessel or an axial liquid velocity within the vessel which is at least three times, for example, from three to five times, the buoyant rise velocity of the largest bubble in the vessel. This results in an extremely high vapor holdup of small bubbles formed by the holes 23 of pipe 21 and the nozzle 24. Furthermore, by maintaining a high recirculation rate within the vessel, bubble coalescence be reduced with the concomitant result that the high interfacial areas that are generated by the holes 23 in mixer 22 are maintained.

Figure 2:
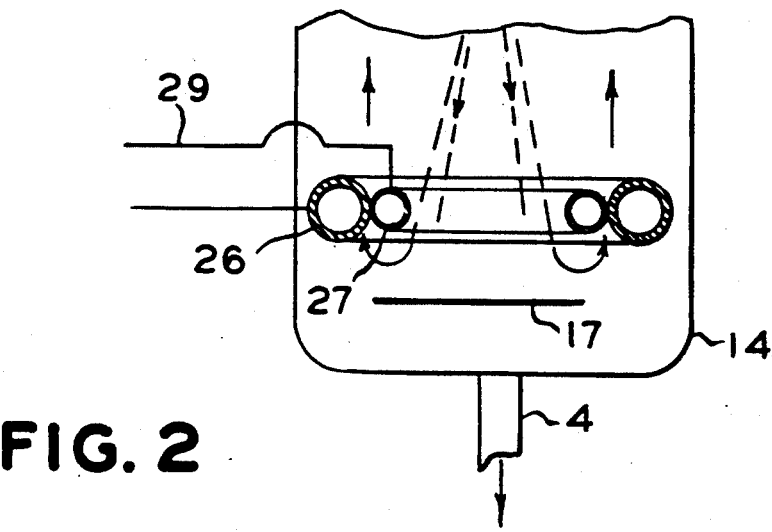
FIG. 2 is a schematic illustration of an alternate aspect of the present invention.

Turning now to FIG. 2, an alternate but particularly preferred embodiment of the present invention is shown. In this embodiment, ring sparger pipes 26 and 27 are located at the lower end of the annular region 16 of vessel 10. Preferably the spargers are located in the annular region 16 sufficiently above baffle 17 so as not to interfere with the downward flow of fluid from central region 15. In operation, a portion of the gaseous olefin is sparged through the annular ring sparger 26 to aid in setting up and maintaining the flow of fluids circulating in vessel 10. Similarly, a portion of the liquid acid is sparged through ring sparger 27 from line 29. Indeed, it is particularly preferred that the openings in the gas spargers be substantially orthogonal to the openings in the liquid sparger as is described in greater detail in copending application Ser. No. 210,550 filed Jun. 21, 1988 now abandoned, which is incorporated herein by reference.

When the ring sparger is used, from about five to about fifty percent of the total amount of gas fed to the vessel, and preferably about ten percent of the gas fed to the vessel is fed in the annular region 16 through the annular sparger 26 providing a buoyancy driving force in the outer annular region 16 that stabilizes the recirculating flow. Typically the volumetric ratio of gas to liquid is in the range of from about 4:1 to about 1:2.

While in the preceding discussion specific mention was made with respect to using a gas and a liquid, in other applications, such as processes involving two distinct liquid phases or two liquid and one gaseous phase, it is preferred to circulate the recycle fluid through a separator drum, particularly where a phase volume ratio enhancement or control is desired over and beyond that available by proportioning the two liquid feeds to the reactor. This technique is described in copending application Ser. No. 235,572 filed Aug. 24, 1988 now abandoned, and is incorporated herein by reference.

What is claimed is:

1. An apparatus for contacting of at least two distinct fluid phases, the apparatus consisting essentially of:
    a vertically disposed vessel for containment of at least two distinct fluid phases, the vessel being defined by a cylindrical wall of a given diameter and defining a cylindrical space, the vessel including a top fluid inlet and a bottom fluid outlet;
    baffle means positioned within the vessel and above the bottom fluid outlet at a distance of about 0.2 to about 0.5 times the diameter of the vessel;
    nozzle means positioned to extend downwardly from the top fluid inlet into the vessel;
    a conduit providing communication between the top fluid inlet and the nozzle means, the conduit including means for generating bubbles of one of the distinct fluid phases in the other and
    for feeding the bubble of one phase in the other through the nozzle means at a velocity sufficient to eject the bubbles of one phase in the other from the nozzle means into the fluid contained in the vessel and to force the fluid phases to flow downwardly through a central region of the vessel and upwardly through an annular region surrounding the central region.

2. The apparatus of claim 1 including means for recycling fluid from the bottom fluid outlet to the top fluid inlet.

3. The apparatus of claim 2 including means for separately introducing two fluid phases in the annular region at the lower end of the vessel.

4. The apparatus of claim 3 wherein the means for separately introducing two fluid phases in the annular region is a double ring sparger.

* * * * *